United States Patent [19]

Elek et al.

[11] 4,441,893
[45] Apr. 10, 1984

[54] ENHANCED CARBON MONOXIDE UTILIZATION IN METHANATION PROCESS

[75] Inventors: Louis F. Elek, Peekskill; Albert C. Frost, Congers, both of N.Y.

[73] Assignee: Union Carbide Corporation, Danbury, Conn.

[21] Appl. No.: 439,635

[22] Filed: Nov. 5, 1982

Related U.S. Application Data

[63] Continuation of Ser. No. 224,441, Jan. 12, 1981, abandoned.

[51] Int. Cl.$^3$ .............................................. C10K 3/04
[52] U.S. Cl. .................................... 48/197 R; 585/733
[58] Field of Search ...................... 585/733; 48/197 R

[56] References Cited

U.S. PATENT DOCUMENTS

| | | | |
|---|---|---|---|
| 2,686,819 | 8/1954 | Johnson | 260/676 |
| 3,031,287 | 4/1962 | Benson et al. | 48/197 |
| 4,242,103 | 12/1980 | Rabo et al. | 585/733 X |
| 4,242,104 | 12/1980 | Frost et al. | 585/733 X |
| 4,351,646 | 9/1982 | Frost et al. | 585/733 X |
| 4,369,131 | 1/1983 | Risch et al. | 585/733 X |

*Primary Examiner*—Thomas A. Waltz
*Attorney, Agent, or Firm*—Alvin H. Fritschler

[57] ABSTRACT

Carbon monoxide - containing gas streams are passed over a catalyst to deposit a surface layer of active surface carbon thereon essentially without the formation of inactive coke. The active carbon is subsequently reacted with steam or hydrogen to form methane. Surprisingly, hydrogen and water vapor present in the feed gas do not adversely affect CO utilization significantly, and such hydrogen actually results in a significant increase in CO utilization.

15 Claims, No Drawings

ENHANCED CARBON MONOXIDE UTILIZATION IN METHANATION PROCESS

STATEMENT

The Government of the United States of America has rights pursuant to Contract No. DE-AC03-78CS40177 awarded by the Department of Energy.

This application is a continuation of our prior U.S. application Ser. No. 224,441 filing date 1/12/81, now abandoned.

BACKGROUND OF THE INVENTION

1. Field of the Invention

The invention relates to the production of methane from carbon monoxide. More particularly, it relates to a methanation process capable of effectively utilizing the CO content of waste effluents as feed gas streams.

2. Description of the Prior Art

The production of low-cost methane as a replacement for natural gas has been the subject of considerable interest in light of the energy requirements of industrial societies throughout the world. The COthane process has been developed in response to such interest and concerns. It is particularly advantageous in that this process is capable of utilizing dilute carbon monoxide-containing gas streams without the necessity for the preliminary concentration that has precluded the use of such streams in conventional techniques for the production of methane from carbon monoxide and hydrogen. Thus, waste streams such as the effluent from blast furnace operations, carbon black off-gas, undergound coal gasification and the like can be effectively utilized for the production of methane although previously unsuitable as useful sources of CO.

The COthane process is a cyclic, essentially two-step process in which a surface layer of active surface carbon is deposited on a catalyst and is then contacted with steam or hydrogen to convert the active surface carbon to methane and carbon dioxide. This essentially two-step process is repeated in cyclic operations without the need for regenerating the catalyst as a necessary additional step of the cyclic operation. Upon separation from carbon dioxide by conventional means, the methane is recovered in the form of low-cost relatively pure product, with the process effectively utilizing the carbon values of dilute carbon monoxide-containing waste gas streams or other such sources of feed gas for the process.

There is, of course, a desire in the art to continually improve the available methanation technology. With respect to the COthane process in particular, it is desirable to develop processing improvements and modifications to enhance the overall process, especially with respect to the utilization of the CO content of the waste gas streams that are of particular value as feed gas streams for the process. It is also highly desirable to assure that the secondary or supporting steps associated with the essentially two-step cyclic process as described above are minimized to further enhance the economic attractiveness of the process and thereby to decrease the cost of the methane product obtained therefrom.

It is an object of the invention, therefore, to provide an enhanced process for the low-cost production of methane from carbon monoxide-containing gas streams.

It is another object of the invention to provide improved utilization of the CO content of feed gas streams used in the cyclic, essentially two-step production of methane.

It is a further object of the invention to enlarge the scope of waste streams suitable for use as an effective source of CO in said cyclic, essentially two-step process.

It is a further object of the invention to reduce the supporting steps to be employed in association with said essentially two-step process, thereby reducing the overall cost of the methane produced thereby.

SUMMARY OF THE INVENTION

The invention is based upon the surprising discovery that the presence of hydrogen in the feed gas stream does not result, under the processing conditions of the COthane process, in the premature conversion of CO to methane during the first step of the two-step operation. To the contrary, the presence of hydrogen has been found to significantly enhance the effective utilization of the CO present in the feed gas stream for the production of relatively pure methane in the cyclic, essentially two-step COthane process.

DETAILED DESCRIPTION OF THE INVENTION

Recognition of the surprising discovery upon which the invention is based enables the COthane process for the production of methane to be used with feed gas streams that might otherwise be disregarded because of what would otherwise have been considered unacceptable quantities of hydrogen. Alternately, CO-containing gas streams containing hydrogen might have been treated to remove the hydrogen content thereof before passing the feed gas to the disproportionation reactor in the first step of the cyclic, essentially two-step COthane process. A process has heretofore been developed for the removal of hydrogen from each feed gas streams by a partial oxidation technique. Such a pretreatment step adds, of course, to the overall cost of the process, thereby somewhat reducing the overall benefits of the process in coverting waste streams to methane at relatively low cost. The alternate choice of not applying the COthane process to CO and $H_2$-containing waste streams, on the other hand, carries with it the consequent loss to waste of the CO content of gas streams that, although necessarily waste streams prior to the development of the COthane process, could effectively be utilized for the production of methane by that process and improvements thereto.

The COthane process to which the present invention relates enables dilute carbon monoxide-containing gas streams, apart from a consideration of the technical and economic consequences of the presence of hydrogen in potential feed streams, to be effectively and efficiently utilized for the economic production of methane. Separation of the carbon monoxide from inert gases present in such dilute carbon monoxide-containing streams is accomplished, in the practice of the present invention, without economic disadvantage vis-a-vis known processes applicable to carbon monoxide-containing gas streams not containing appreciable quantities of inert gases. The COthane process is of significance, therefore, not only as a process for the production of low-cost methane but as a process uniquely capable of utilizing carbon monoxide available in gas streams not previously suitable as feed streams for the commercial production of methane.

The process includes the passing of a carbon monoxide-containing gas stream over a suitable catalyst under conditions such that the carbon monoxide is decomposed to form carbon dioxide and active surface carbon, designated as C* and deposited as a surface layer on said catalyst, according to the reaction:

$$2CO \rightarrow CO_2 + C^*. \quad (1)$$

The carbon dioxide and inert gases present in the feed stream are vented from the surface layer of active surface carbon, which is thereafter converted to methane by contact with steam as follows:

$$2C^* + 2H_2O \rightarrow CH_4 + CO_2. \quad (2)$$

The carbon efficiency of the process can be illustrated by the overall reaction (3) below that represents the total reactions (1) and (2) as performed in the practice of the present invention:

$$4CO + 2H_2O \rightarrow 3CO_2 + CH_4. \quad (3)$$

Thus, 4 moles of CO are required for the production of one mole of methane in the stoichiometric relationship illustrated by reaction (3). The COthane process is capable of recovering methane in amounts representing at least about 50% of the stoichiometric amount and, in preferred embodiments, at least about 80% and up to nearly 100% of said stoichiometric amount. Upon separation from the accompanying $CO_2$ by conventional means, therefore, methane is recovered in the form of a low-cost, relatively pure product with the carbon values thus recovered being at least about 12.5% and up to nearly 25% of the carbon present in the carbon monoxide decomposed upon contact with the disproportionation catalyst.

Gas streams containing from about 1 to 100% by volume carbon monoxide can be utilized as the feed stream in the practice of the COthane process. The process is uniquely capable of utilizing carbon monoxide in gas streams not suitable for known methanation techniques because of relatively high concentrations of inert gases therein. Gas streams containing carbon monoxide in amounts of from about 5% to about 50% by volume and containing at least about 5% by volume of nitrogen represent sources of carbon monoxide not previously suitable for commercial methanation operations that are highly suitable for use in the process. Those skilled in the art will readily appreciate that feed gas streams should be sufficiently free from catalyst poisons to ensure adequate catalyst lifetimes. Thus, sulfur impurities should be present in very low concentrations, e.g., less than 1 ppm, preferably less than 0.2 ppm. Conventional techniques are available in the art for removing sulfur impurities as required. If hydrogen or water vapor is also present in the feed gas stream, it has heretofore been believed, and thermodynamic considerations appeared to confirm, that such gases would be converted, partially or completely, to methane by reaction with carbon monoxide under the reaction conditions. The carbon monoxide remaining after such reaction with hydrogen or water vapor would remain to be decomposed to active surface carbon and carbon dioxide in accordance with reaction (1) above. For this reason, the hydrogen and water vapor was preferably limited in the feed gas stream to quantities of less than 10% by volume based on the amount of carbon monoxide present in the gas stream. It was also the contemplation of those skilled in the art to effectively utilize any methane formed during the carbon monoxide decomposition step for heat generation purposes to improve the overall economics of the methanation process in such embodiments in which relatively small amounts of hydrogen present in the feed gas reduced the amount of CO that could be converted to active surface carbon in accordance with reaction (1) above. Carbon monoxide-containing waste gas streams containing appreciable quantities of hydrogen were more generally considered unsuited for use as feed streams for the COthane process without the incorporation of a pretreatment step for the removal of such hydrogen from the carbon monoxide-containing gas stream. Such hydrogen removal can conveniently be accomplished by a pre-methanation step. Furthermore, under the contract referred to above, a partial oxidation process was also developed for the removal of hydrogen from such carbon monoxide-containing feed gas streams prior to the passage of such streams to the disproportionation reactor for the first step of the COthane process. The surprising discovery of the present invention enables gas streams containing both carbon monoxide and hydrogen to be used in the COthane process at enhanced CO utilization and without the pretreatment for removal of hydrogen previously considered necessary before streams having appreciable quantities of such hydrogen could be used in the cyclic, essentially two-step COthane process.

The carbon monoxide decomposition step, in which the carbon monoxide present in the feed gas stream is decomposed to form a surface layer of active surface carbon deposited on a disproportionation catalyst, effectively serves to concentrate the carbon values to be converted to methane, regardless of the carbon monoxide content of the feed gas stream. Dilute carbon monoxide-containing gas streams can be readily employed, therefore, without the necessity for the prior concentration of the carbon monoxide as would be required in conventional techniques. The removal of the carbon dioxide formed as a result of carbon monoxide decomposition, together with the inert gases that may be present in the gas stream, from the catalyst having the surface layers of active surface carbon to be converted to methane is readily carried out inherently in the diproportionation step prior to said active surface carbon conversion in the second chemical step of the essentially two-step COthane process. The use of a dilute carbon monoxide-containing gas stream thus does not require the prior separation of the carbon-monoxide content thereof from inert gases as would be required in conventional methanation techniques. This ability to utilize dilute carbon monoxide-containing gas streams constitutes a major advance in the art, permitting the production of low-cost methane from gas streams not capable of practical utilization for the economic production of methane by presently available techniques. This capability is enhanced by the present invention, enabling greater CO utilization, and hence serving to reduce the cost of the overall operation, while avoiding the cost of pretreatment of the feed to render the feed gas suitable for the COthane process.

The decomposition of carbon monoxide over a disproportionation catalyst is carried out, in the practice of the invention, at a reaction pressure of from about 1 to about 10 atmospheres and at a reaction temperature of from about 100° C. to about 350° C., preferably between about 200° C. and about 350° C. with space velocities generally of from about 1000 to about 30,000 hr$^{-1}$. Since the most useful product of the carbon monoxide decomposition, for purposes of the invention, is the solid surface layer of active surface carbon, it will usually be to no advantage to carry out the decomposition reaction at pressures much above atmospheric. Particularly in light of the presence of hydrogen in the feed gas of the present invention, the pressure employed for the CO decomposition step, i.e., the first step of the COthane process, should preferably be in the range of from about 1 to about 4 atmospheres.

In the practice of the Cothane process, the carbon monoxide-containing gas stream is passed over the catalyst for a time sufficient to deposit a surface layer of active surface carbon on the catalyst essentially without the formation of inactive coke thereon. Such inactive coke is not only itself inert under the methanation reaction conditions of the invention, but may tend to reduce the capacity of the catalyst to form active surface carbon in subsequent operations. For practical commercial applications of the invention, such subsequent oprations, involving the cyclic use of the catalyst for the disproportionation of additional quantities of CO, are desirably carried out at reaction temperatures above about 100° C. and preferably within said preferred range of from about 200° C. to about 350° C., more preferably from about 260° C. to about 310° C. in the practice of the present invention. It will be understood that said CO disproportionation temperature refers to the average temperature of the reaction bed. It will also be understood by those skilled in the art that the particular reaction temperature pertaining to any given commercial application of the invention will be subject to inevitable variations depending on the type of operation employed, e.g., fixed or fluid bed, and on the capability of temperature control equipment employed in such commercial application of the invention. The reaction temperature may exceed the indicated preferred temperature limits on a transitory basis without departing from the scope of the invention although, for enhanced economic and technical practicability of commercial applications, the average reaction bed temperature should desirably be within the preferred range indicated above, i.e., from about 200° C. up to about 350° C. At higher temperatures, the suitability of the catalyst for use in the cyclic two-step process of the invention is diminished so that the overall efficiency of the process is adversely effected, and the cost thereof increased, at such less favorably operating conditions.

It should be noted that the active surface carbon formed in the practice of the COthane process is quite distinct from the inactive coke formed if the carbon monoxide decomposition is allowed to proceed beyond the maximum level of active surface carbon deposition. Such inactive coke is known in the art as an undesired potential deposit on catalyst surfaces from carbonaceous feeds employed in various methanation operations. Such coke has essentially the reactivity of graphitic carbon. Its reaction with steam, for example, requires temperatures in the range of from about 600° C. to about 1000° C. This reaction, which is the well-known water gas reaction, produces CO and H$_2$ as its principal products. The active surface carbon of the present invention, on the other hand, reacts with steam at appreciably lower temperature levels to provide methane as its principal product in accordance with equation (2) above. While the prior art is concerned with the avoidance of the undesired deposition of inactive coke on catalytic surfaces, the COthane process utilizes the deposition of active surface carbon, without formation of inactive coke, to produce methane by the low-cost process as described herein.

The amount of active surface carbon deposited will depend upon the surface area of the disporportionation catalyst and the operating conditions employed. Relatively low temperatures and the shortest possible residence time tend to favor the formation of the active surface carbon. Under some circumstances, particularly at higher temperatures within the operable range or with a very long residence time, the presence of CO in the gaseous effluent denotes a relatively sharp demarcation point between the deposit of the desired active surface carbon and the undesired deposition or other formation of inactive coke on the surface of the catalyst. In determining the amount of active surface carbon that can be deposited on the catalyst, therefore, the point at which CO breakthrough occurs has been taken as a practical indicator of the maximum level of active surface carbon deposition in the COthane process. It will be understood, however, that said maximum level of deposition must be determined, for any particular embodiment, by the particular operating conditions employed, the specific catalyst utilized and the available surface area of the catalyst as applied in such embodiment. While higher pressures for the CO decomposition step can generally be employed in the practice of embodiments of the COthane process in which hydrogen is not present in the feed gas, the relatively low pressures indicated above for the practice of the present invention, combined with short residence conditions for the disproportionation step, result in the hydrogen present in the feed gas reacting with the carbon monoxide to form additional active surface carbon. It is believed that this additional formation of active surface carbon, which enhances the CO utilization of the process over that ordinarily achieved in the practice of the COthane process, occurs as a result of the reaction:

$$CO + H_2 \rightarrow C^* + H_2O \tag{4}$$

Reaction (4) occurs very rapidly, while the previously anticipated reaction of carbon monoxide or active surface carbon with hydrogen to form methane occurs less rapidly, although faster than the undesired conversion of active surface carbon to coke. The disproportionation step of the present invention is carried out, therefore, by passing the CO and H$_2$ containing gas stream over the catalyst for a time sufficient to deposit a surface layer of active surface carbon on the catalyst essentially without the formation of methane or of the formation of active surface carbon on the catalyst. The formation of methane can readily be detected by evaluation of the effluent removed from the disproportionation reactor. Under the low pressure, short residence time conditions of the invention, therefore, the surprising increase in CO utilization enhances the overall process and eliminates the need for a hydrogen removal system for hydrogen-containing feed streams to the COthane process.

The COthane process in general, and the invention in particular, utilizes a catalyst capable of catalyzing the disproportionation of carbon monoxide. The transition metals including and to the left of nickel in the third row of the Periodic Table; including and to the left of rhodium in the fourth row thereof; and including and to the left of iridum in the fifth row thereof are capable of catalyzing said disproportionation. Preferred catalysts include nickel, cobalt, iron, ruthenium, rhenium and alloys thereof, with nickel and cobalt being most preferred on an overall technical-economic basis. For purposes hereof, it will be understood that the catalyst shall include the metallic form, the oxide form, or any other suitable form of the particular catalyst employed. As the active surface carbon will be deposited in a surface layer while assuring thatthe decomposition reaction does not proceed to the point of methane or of inactive coke formation, a high catalyst surface area is advantageous to achieve a high surface carbon loading, enhancing the economics of the process. The catalyst employed will preferably have a surface area of at least about 10 $m^2/gr$, with surface areas of at least about 25 $m^2/gr$ being more preferred. In some embodiments, the catalyst may have an even higher surfce area, i.e., of at least about 50 $m^2/gr.$, it being appreciated that such high surface areas contribute to the attractiveness of the invention on an overall technical and economic basis. It will also be appreciated that the catalyst will generally be employed in combination with catalyst support additives and/or binding agents to assure that the catalyst has and maintains a desired combination of activity, capacity and stability for use in practical fixed or fluid bed commercial operations. It will also be understood that the surface area of the catalyst, as referred to herein, relates to the B.E.T. surface area of the catalyst composition measured after the combination of the catalyst with such additives or agents and after reduction of the catalyst to its active state.

For the economic production of methane in practical commercial operations, it is highly desirable that the catalyst be capable of use in the essentially two-step, cyclic, low-cost process of the invention without the need for regeneration following each reaction cycle. Furthermore, the catalyst should advantageously be capable of effective continued use in the cyclic two-step process of the invention over as long a cycle period as possible prior to regeneration to enhance the economic feasibility of the process in such commercial operations. For such cyclic operations that are inherently part of the economic attractiveness of the invention, the catalyst will, in particularly preferred embodiments, be employed essentially in its metal state and will be taken from especially preferred catalysts, including nickel, cobalt, ruthenium, rhenium and alloys thereof, with nickel and cobalt being most preferred on an overall technical-economic basis to enhance the cyclic feature inherent in the overall advantages of the two-step process of the invention. It will be understood by those skilled in the art that such catalysts, in their metal state, are not generally available in a totally pure form but may contain small amounts of oxygen. The especially preferred catalysts enhancing the cyclic, two-step process of the invention will be substantially in the metal state rather than in oxide form. It will be noted that iron is not included among the especially preferred catalysts for practical commercial operation of the two-step, inherently cyclic process of the invention, since iron is considerably less reactive to CO in the initial disproportionation step than is the most preferred nickel and cobalt catalysts. In the active surface carbon conversion step, the iron is found to react with steam to form an oxide that may be inert or relatively inactive for carbon monoxide disproportionation depending on the valance state of the iron in said oxide. In addition to the generally less desirably nature of the use of catalysts in the oxide form, therefore, it may be necessary to convert the iron oxide catalyst to iron metal form as a separate and necessary additional step of the cyclic process. Such a requirement would, of course, change the process from one having two essential chemical steps, repeated on a cyclic basis, to a process having three essential chemical steps. As indicated above, the economic and technical advantages of the inherently cyclic process of the invention would not be realized in embodiments of commercial operations in which iron, in such oxide form, is emloyed as the disproportionation catalyst.

As indicated above, inert gases present in the carbon monoxide-containing feed gas stream, together with gases formed during carbon monoxide decomposition, are vented from the reaction zone in which a surface layer of active surface carbon is deposited on the disproportionation catalyst. As a result, the carbon values in the carbon monoxide that are to be converted to methane are separated from said inert gases inherently in the practice of the invention. No prior concentration of the carbon monoxide present in dilute carbon monoxide-containing gas streams, and no separation of said carbon monoxide from inert gases such as nitrogen and argon present in said gas streams, is required. It is such requirements and the cost thereof that effectively preclude the use of dilute carbon monoxide-containing gas streams in prior art methanation techniques. The present invention achieves, in effect, such concentration essentially without a cost penalty compared to alternative processes that utilized gas streams containing a relatively high proportion of carbon monoxide therein to avoid the necessity for employing a prohibitively costly cryogenic or other separation of inerts. The present invention is particularly advantageous and achieves a major advance in the art in permitting the methanation of dilute carbon monoxide and hydrogen-containing gas streams and a relatively high proportion of inerts, e.g., the indicated gas streams containing from about 5% to about 70% by volume nitrogen.

The active surface carbon deposited on the catalyst, following the venting of inert gases therein, is contacted with steam or a steam-containing gas stream to convert said active surface carbon to methane and $CO_2$ in accordance with reaction (3) above. Reaction temperatures of from about 100° C. to about 400° C. may be employed, with conversion temperatures of from about 200° C. to about 350° being generally preferred. The conversion of active surface carbon by steam may be carried out at reaction pressures of from about 1 to about 100 atmospheres. By using high pressure steam for the active surface carbon conversion, the generation of a high pressure produce gas stream is achieved without the need for expensive compression equipment and high energy consumption, further enhancing the economic attractiveness of the process. Thus, steam is the especially preferred reactant for conversion of the active surface carbon to methane in practical commercial operations in which the inherently cyclic, two-step process of the invention is carried out for the methanation of CO-containing gas streams on an economically attractive basis.

While the conversion of active surface carbon to methane can be accomplished by contacting the surface layer of said carbon with hydrogen or a hydrogen-containing gas under the operating conditions above for conversion by steam, the use of steam is preferred because of the costs associated with the generation of hydrogen. The CO$_2$ formed in said conversion by steam can readily be separated from the methane, if desired, by well known commerically available techniques to provide a relatively pure, low-cost methane product. The Benfield aqueous alkaline scrubbing process and the Shell Sulfinol and Allied Chemical Selexol solvent extraction processes are examples of commercial techniques for removing carbon dioxide and other acid gases from gas streams.

The disproportionation catalyst will typically be mixed with a catalyst support additive or with binders to assure that the catalyst has a desired combination of activity, capacity and stability. In the absence of such additives and/or binders, nickel, for example, is relatively unstable and tends to agglomerate and sinter with resultant reduction of its surface area.

It is within the scope of the invention to employ any available support additive material capable of supporting and/or dispersing the catalyst, so as to prevent agglomeration and sintering thereof, and thus to enhance the activity and capacity of the catalyst in continuous commercial operations. Such support additives will generally be employed in varying amounts ranging from about 0.1% to about 50% by weight of additive based on the weight of catalyst composition mixture of catalyst and additive. Examples of suitable additives are zirconia, thoria, alumina, silica and mixtures thereof, although various other materials, such as rare earth oxides, may be employed for the indicated catalyst support purposes. In particular embodiments of the invention, the additive is employed in an amount within the range of from about 3% to about 15% by weight based on the weight of the catalyst composition mixture. Zirconia, alumina and silica are preferred catalyst support additives with zirconia being generally most preferred.

It will be understood that various combinations of such support additive materials, with or without binding agents, may be employed to achieve desired support and/or dispersion of the disproportionation catalyst employed in particular embodiments of the process of the invention. For example, it has been found advantageous to employ a combination of zirconia and alumina support additives. Each additive may preferably be employed in an amount within the range of from about 3% to about 30% by weight of the catalyst composition mixture of catalyst and additive, with the combination being employed in an amount up to about 50% by weight based on the weight of said catalyst composition. As indicated above, nickel is the generally preferred catalyst, with the surface area of the catalyst being generally at least about 10 m$^2$/gr, and preferrably at least about 25 m$^2$/gr more preferably at least about 50 m$^2$/gr. Binding agents, if employed, will generally be mixed with the catalyst composition in an amount within the range of from about 5% to about 40% by weight of such binding agent based on the total weight of the catalyst composition-binder mixture. Various binding agents known in the art may be employed in a conventional manner as will readily be appreciated by those skilled in the art. Boehmite alumina, a hydrous aluminum oxide, and colloidal silica are readily available binders.

While various catalyst-support additive combinations suitable for other purposes of the invention may readily be determined by those skilled in the art, it has been found particularly convenient to employ a coprecipitated mixture of catalyst and catalyst support additive. Thermally stable coprecipitated catalysts useful for methanation reactions have heretofore been known in the art as evidenced, for example, by the Hansford patent, US 3,988,263 that relates to combinations of alumina with catalytic materials such as nickel. The catalyst support additive, in such embodiments, constitutes generally the hydroxide or carbonate form thereof coprecipitated with the hydroxide or carbonate of the catalyst material prior to the reduction of said catalyst hydroxide or carbonate to the active catalyst state. For purposes of the present invention, the catalyst should comprise from about 50% to about 90% of the catalyst composition mixture of catalyst and additive. Nickel and cobalt are preferred catalysts, with silica being the preferred catalyst support additive although it will be appreciated that alumina, zirconia or other suitable support additives can also be employed.

While the invention necessarily includes two basic chemistry process steps, repeated on a cyclic basis, it will be understood that various processing steps, or unit operation steps, may be carried out incidental to the essential features of the invention. Thus, it was noted above that pretreatment of the feed may be employed to remove sulfur impurities or carbon dioxide or the like. In addition, by-product carbon dioxide formed during conversion of active surface carbon with steam in accordance with reaction (2) is separated from product methane by conventional techniques. It will be understood by those skilled in the art that various other processing steps incidental to the heart of the present invention may be employed in practical applications of the invention. Accordingly, small adjustments in reaction temperature may be made, as by heating or cooling the reaction zone, and a purge gas at a desired temperature, e.g., about 240° C., may be passed through said zone to achieve a desired cooling effect. It will also be understood that, during repeated cycles of the cyclic, basically two-step process of the invention, the disproportionation catalyst becomes coated with carbon that eventually reduces the efficiency of the catalyst to the point where catalyst regeneration becomes necessary or desirable. Oxidation regeneration can be employed to burn off said carbon so as to regenerate the catalyst for subsequent use in the cyclic, two-step methanation process of the invention. Such regeneration can be conveniently carried out in situ in the reaction zone.

As noted above, many CO-containing waste gas streams, which are potential feed streams for the COthane process, contain varying amounts of hydrogen and water that would be expected to react with the active surface carbon or with CO and thus reduce the CO utilization of the process. For purposes of this invention, the term "CO utilization" will be understood to means the amount of methane produced/the amount of CO consumed. The expectations of lower CO effeciencies was justified upon calculation of the thermodynamic equilibrium for such mixtures under COthane process conditions. For example, a feed gas containing 0.25 grams moles of CO, 0.05 gram moles of water and 0.7 gram moles of nitrogen was expected by such calculations to form only 0.085 gram moles of active surface carbon, whereas 0.125 gram moles of such carbon would be expected to form if no water were present. Thus, more feed gas would be required to deposit active surface carbon up to the full potential of the catalyst, in turn lowering the CO utilization of the process. Similar results have been shown in calculations based on feed streams containing 5-10 mole % hydrogen, confirming the expectations of lower CO utilization. Thermodynamic calculations further show that if both hydrogen and water are present in relatively large amounts, as for untreated, cooled carbon black off-gas, no active surface carbon at all would be expected to form. In fact, such a mixture would be expected to be a net active surface carbon consumer, indicating that the COthane process would not operate with untreated carbon black off-gas.

In a series of experimental runs, these equilibrium-based expectations were compared with generated data using unregenerated catalyst and various hydrogen and water-containing feed streams. The CO utilization of a feed stream containing 5–10 mole % water was found to be only slightly affected by the presence of water. Thus, a decrease of about 3% in CO utilization was observed, as compared with a 32% decrease predicted by equilibrium calculations.

The CO utilization of hydrogen-containing feed streams was surprisingly discovered to actually increase rather than to decrease as would commonly have been expected by the general knowledge in the art and thermodynamic calculations. As shown in the Table I below, the CO utilization in particular experimental runs for a feed stream containing 5–10% by volume hydrogen actally increased by 26–41% rather than decreasing by 17–29% as predicted by equilibrium calculations:

TABLE I

EFFECT OF HYDROGEN ON METHANE EFFICIENCY
Using nickel catalyst, a maximum
disproportionation temperature of about 300° C., a feed
gas flowrate of 24 L/min, with a 1½ minute cycle and
a disproportionation pressure of about 20 psig.

| Feed Gas Comp. | In Disprop. Effluent | | In Steam Effluent | | CO Utilization % (4) (100) (1), (2), (3), & (4) |
|---|---|---|---|---|---|
| | $CO_2^{(1)}$, ml | $CH_4^{(2)}$, ml | $CO_2^{(3)}$, ml | $CH_4^{(4)}$, ml | |
| 25% CO 75% N$_2$ | 1200 | 45 | 1100 | 600 | 20.4 |
| 25% CO 5% H$_2$ 70% N$_2$ | 1000 | 60 | 1250 | 800 | 25.7 |
| 25% CO 75% N$_2$ | 1200 | 10 | 1300 | 580 | 18.8 |
| 25% CO 10% H$_2$ 65% N$_2$ | 800 | 70 | 1350 | 800 | 26.5 |

The surprising improvement in CO utilization was further shown for a simulated carbon black off-gas feed stream combining hydrogen and water as set forth in Table II below:

TABLE II

CO EFFICIENCY WITH SIMULATED CARBON BLACK OFF-GAS
Using nickel catalyst, a maximum
disproportionation temperature of about 305° C. for the
first run and 337° C. for the second, a feed gas flowrate of
24 L/min, with a 1½ minute cycle and a
disproportionation pressure of about 20 psig.

| Feed Gas Comp. | In Disprop. Effluent | | In Steam Effluent | | CO Utilization % (4) (100) (1), (2), (3), & (4) |
|---|---|---|---|---|---|
| | $CO_2^{(1)}$, ml | $CH_4^{(2)}$, ml | $CO_2^{(3)}$, ml | $CH_4^{(4)}$, ml | |
| 15% CO 15% H$_2$ 5% H$_2$O 65% N$_2$ | 450 | 130 | 1125 | 600 | 26.0 |
| 15% CO 15% H$_2$ 5% H$_2$O 65% N$_2$ | 250 | 520 | 850 | 600 | 27.0 |

The 26–27% CO for such a carbon black off-gas stream is well above the about 20% utilization for hydrogen and water-free streams as indicated above. Even more surprising and significant, such utilization can be compared with the zero CO utilization that would be predicted by equilibrium calculations for such streams.

The data above indicates that equilibrium is not reached at the low pressure of the disproportionation step during the short time required for the feed gas to pass through the reactor. It is believed that the relatively fast reaction (4) above occurs during the short residence time. This permits one gram mole of active surface carbon to form from one gram mole of CO, instead of from two gram moles of CO as is required by disproportionation reaction (1) above. This lower CO consumption results in the high CO utilization observed. It is also believed that the reactions involving water, i.e., reaction 5 below:

$$2C^* + 2H_2O \rightarrow CH_4 + CO_2, \tag{5}$$

are relatively slow at the low pressures employed in the disproportionation step of the invention. This enables a feed gas with a relatively high CO concentration and about 100° F. dew point to be sent to the COthane process unit without employing a preliminary drying step. In the practice of the invention it will be understood that the feed gas stream, containing hydrogen or hydrogen and water, is passed over the catalyst for a time sufficient to deposit a surface layer of active surface carbon pursuant to reaction (1) and (4) above essentially without the formation of methane by the slower reaction (5) and without the formation of inactive coke on the catalyst.

The invention is thus highly advantageus in the use of CO-containing gas streams containing hydrogen therein. The content of hydrogen present in particular embodiments of the invention may range from about 5% to about 100% or more by volume based on or relative to the volume of CO present in said stream. Potential feed gas streams having a hydrogen concentration of from about 20% to about 100% by volume based on the volume of CO in said stream are particularly advantageous. As in the basic COthane process, diluted CO-containing gas streams containing from about 5% to about 50% by volume carbon monoxide, including commercially available waste gas streams having a CO concentration of from about 15% to about 25% by volume, based on the total volume of the gas feed to the COthane unit, can readily be employed in the practice of the invention.

The surprising findings upon which the invention were based will indicate to those skilled in the art that CO and hydrogen-containing waste gases, such as the potentially large amount of cooled carbon black off-gas, can be considered as an attractive potential feed gas for the COthane process and such consideration need not be based on the technical necessity for employing a costly hydrogen removal step prior to the passage of the feed gas to the disproportionation step of the process. Not only can the hydrogen removal step be eliminated, but such elimination of what previously would have been considered a necessary or desirable step can be expected to result in a very significant increase in CO utilization, e.g., the about 25% increase noted above. This enables the methane production rate to be increased by a factor of about 25%, while the cost of the methane production is decreased by a factor of about 25% in the practice of the invention. The invention represents, therefore, a major advance in the development of the COthane process, one that contributes significantly to the scope of application to available waste streams and the technical and economic feasibility of employing said streams for the production of low-cost methane.

Therefore what is claimed is:

1. A cyclic process for the production of methane from carbon monoxide-containing gas streams comprising:
    (a) passing a carbon monoxide-containing feed gas stream over a catalyst present in a metal state and capable of catalyzing the disproportionation of carbon monoxide at a temperature of from about 100° C. to about 350° C. and a pressure of from about 1 to about 10 atmos., said feed gas stream having a hydrogen concentration of from about 5% to about 100% by volume based on the volume of CO present in said stream, and being passed over the catalyst for a time sufficient to deposit a surface layer of active surface carbon on the catalyst essentially without the formation of inactive coke on the catalyst, the residence time of the feed gas stream in the presence of the catalyst being sufficiently short so as to enable hydrogen present in said feed gas stream to react with the carbon monoxide content of said feed gas stream to form additional active surface carbon essentially without the formation of methane by the less rapid reaction of active surface carbon or carbon monoxide with hydrogen present in the feed gas stream;
    (b) contacting said layer of active surface carbon deposited on said catalyst present in the metal state with steam, a steam-containing gas stream or hydrogen at a pressure of from about 1 to about 100 atmos., and a temperature of from about 100° C. to about 400° C., thereby converting said active surface carbon to methane and carbon dioxide; and
    (c) passing additional carbon monoxide-containing gas over said catalyst from step (b) and repeating said steps (a) and (b) on a cyclic basis, whereby relatively pure methane can conveniently be produced from carbon monoxide-containing gas streams on a cyclic basis, the presence of said hydrogen at the relatively low disproportionation pressures employed in step (a), for said short residence time, surprisingly enhancing the effective CO utilization and the overall technical-economic feasibility of the methanation process.

2. The process of claim 1 in which said CO decomposition pressure is from about 1 to about 4 atmospheres.

3. The process of claim 1 in which said carbon monoxide decomposition temperature is from about 200° C. to about 350° C.

4. The process of claim 3 in which said temperature is from about 260° C. to about 310° C.

5. The process of claim 1 in which said hydrogen concentration is from about 20% to about 100% by volume based on the volume of CO in said stream.

6. The process of claim 5 in which said carbon monoxide decomposition pressure is from about 1 to about 4 atmos.

7. The process of claim 6 in which said carbon monoxide decomposition temperature is from about 200° C. to about 350° C.

8. The process of claim 1 in which said gas stream contains from about 5% to about 50% by volume carbon monoxide.

9. The process of claim 8 in which said gas stream contains from about 15% to about 25% by volume carbon monoxide.

10. The process of claim 8 in which said carbon monoxide decomposition pressure is from about 1 to about 4 atmos.

11. The process of claim 10 in which said carbon monoxide decomposition temperature is from about 200° C. to about 350° C., and said conversion of active surface carbon by steam is at a temperature of from about 200° C. to about 350° C. and a pressure of from about 100 to about 500 psi.

12. The process of claim 1 in which said gas stream comprises carbon black off-gas.

13. The process of claim 11 in which said carbon monoxide decomposition temperature is from about 260° C. to about 310° C.

14. The process of claim 13 in which said disproportionation pressure is about 20 psig.

15. The process of claim 2 in which said CO decomposition pressure is about 20 psig.

* * * * *